United States Patent
Chang et al.

(10) Patent No.: US 6,474,138 B1
(45) Date of Patent: Nov. 5, 2002

(54) ADSORPTION BASED CARBON MONOXIDE SENSOR AND METHOD

(75) Inventors: Chin H. Chang, Palatine, IL (US); Ulrich Bonne, Hopkins, MN (US); Richard A. Alderman, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 36 days.

(21) Appl. No.: 09/724,536

(22) Filed: Nov. 28, 2000

(51) Int. Cl.⁷ .............................................. G01N 25/48
(52) U.S. Cl. ..................... 73/25.01; 73/25.05; 73/23.31; 73/31.05
(58) Field of Search ............................. 73/23.31, 25.01, 73/25.05, 31.05

(56) References Cited

U.S. PATENT DOCUMENTS

| | | |
|---|---|---|
| 4,343,768 A | 8/1982 | Kimura |
| 4,379,402 A | 4/1983 | Harman, III |
| 4,478,077 A | 10/1984 | Bohrer et al. |
| 4,501,144 A | 2/1985 | Higashi et al. |
| 4,624,137 A | 11/1986 | Johnson et al. .......... 73/204.19 |
| 4,651,564 A | 3/1987 | Johnson et al. |
| 4,683,159 A | 7/1987 | Bohrer et al. |
| 4,696,188 A | 9/1987 | Higashi ................... 73/204.26 |
| 4,914,742 A | 4/1990 | Higashi et al. |
| 4,944,035 A | 7/1990 | Aagardl et al. |
| 4,956,793 A | 9/1990 | Bonne et al. |
| 5,038,304 A | 8/1991 | Bonne |
| 5,177,696 A | 1/1993 | Bonne |
| 5,235,844 A | 8/1993 | Bonne et al. |
| 5,252,949 A | 10/1993 | Kirby et al. |
| 5,351,029 A | 9/1994 | Huth et al. |
| 5,515,714 A | 5/1996 | Sultan et al. |
| 5,535,135 A | 7/1996 | Bush et al. |
| 5,629,474 A | 5/1997 | Williams |
| 5,670,949 A | 9/1997 | Kirby et al. |
| 5,813,764 A * | 9/1998 | Visser et al. ................ 73/25.05 |
| 5,852,308 A | 12/1998 | Wood |
| 5,861,545 A | 1/1999 | Wood |
| 5,869,749 A | 2/1999 | Bonne et al. |
| 5,892,140 A | 4/1999 | Wood |
| 5,925,476 A | 7/1999 | Kawatsu |
| 5,948,965 A * | 9/1999 | Upchurch et al. ......... 73/23.31 |
| 6,001,499 A | 12/1999 | Grot et al. |
| 6,071,476 A | 6/2000 | Young et al. |
| 6,090,268 A | 7/2000 | Kunimatsu et al. |
| 6,240,371 B1 | 5/2001 | Azar ......................... 73/23.31 |
| 6,318,150 B1 | 11/2001 | Temple |

FOREIGN PATENT DOCUMENTS

| | | | | |
|---|---|---|---|---|
| GB | 2103806 | * | 2/1983 | ................ 73/25.05 |
| JP | 63-169547 | * | 7/1988 | ................ 73/25.05 |
| JP | 4-47228 | | 2/1992 | |

OTHER PUBLICATIONS

Article entitled: "Motorola's MEMS–Based High Performance Carbon–Monoxide Sensor", Jan. 28, 1997.

Article entitled: "New Method for Gas Identification Using a Single Semiconductor Sensor", Takada et al., *Sensors and Actuators B*, 66 (2000) 22–24.

(List continued on next page.)

*Primary Examiner*—Daniel S. Larkin
(74) *Attorney, Agent, or Firm*—Andrew A. Abeyta; Trevor B. Joike

(57) ABSTRACT

A carbon monoxide sensor and method is shown and described. The sensor includes a sensing element that includes an adsorbent dispersed over a support material. The adsorbent is capable of exothermically adsorbing carbon monoxide. The sensor also includes a temperature sensor in contact with the sensing element and a signal processing module coupled to the temperature sensor. The temperature sensor communicates signals indicative of a temperature increase of the sensing element to the processing module, thereby indicating an adsorption and, therefore, a presence of carbon monoxide.

21 Claims, 1 Drawing Sheet

OTHER PUBLICATIONS

Article entitled: "Fabrication and Properties of a Si–Based High–Sensitivity Microcalorimetric Gas Sensors", Zanini et al., *Sensors and Actuators A*, 48 (1995) 187–192.

Article entitled: "Temperature Drop of Semiconductor Gas Sensor When Exposed to Reducing Gases—Simultaneous Measurement of Changes in Sensors Temperature and in Resistance", Tadashi Takada, *Sensors and Actuators B*, 66 (2000) 1–3.

Article entitled: "Catalytic Calorimetric Gas Sensors", Visser et al., $5^{th}$ *Int'l. Mtg. on Chemical Sensors, Rome, Italy*, Jul. 11–14, 1994 Proceedings, p. 468.

Article entitled: "Design of a Low Power $SnO_2$ Gas Sensor Integrated on Silicon Oxynitride Membrane",Astié et al., *Sensors and Actuators B*, 67 (2000) 84–88.

* cited by examiner

ADSORPTION BASED CARBON MONOXIDE SENSOR AND METHOD

TECHNICAL FIELD OF THE INVENTION

The present invention relates generally to gas sensors and, more particularly, to carbon monoxide sensors.

BACKGROUND OF THE INVENTION

Carbon monoxide sensors are used in a wide variety of applications, including the monitoring of heating installations that employ fossil fuels as an energy source and the monitoring of exhaust fumes from internal combustion engines. Two additional applications involve self-cleaning ovens and fuel cells.

Specifically, self-cleaning ovens include a cleaning cycle that removes carbonaceous residues through a high-temperature burning at a high-power capacity for a fixed amount of time. Because the high-temperature burning consumes a relatively large quantity of energy, there is a need for efficient self-cleaning cycles that automatically shut off the oven as soon as the burning process is complete. One way to accomplish this would be to monitor the carbon monoxide evolution during the heating cycle. Specifically, it is known that a typical dirty oven, when being cleaned at temperatures exceeding 800° F., will begin to emit carbon monoxide at a temperature of about 550° F. The amount of carbon monoxide being emitted will peak at around 800° F. at a value of about 1500 ppm. After this peak value is reached, the carbon monoxide concentration decreases to around 200 ppm at the end of the cycle. An appropriate shut down point will occur for a typical oven at a carbon monoxide concentration of about 200 ppm.

Therefore, there is a need for a robust, high-sensitivity carbon monoxide sensor to monitor self-cleaning oven cycles and other carbon monoxide emitting devices. Further, the sensor must be sensitive so as to detect a relatively low concentration of carbon monoxide of less than 50 ppm.

Currently-available carbon monoxide sensors include infrared adsorption sensors and thin film metal oxide technology, such as tin oxide sensors. The infrared adsorption sensors are inappropriate for the household oven market due to their high cost and low sensitivity. The thin film metal oxide sensors are also inappropriate for use in monitoring self-cleaning oven cycles because they generally don't work well in a humid environment. Further, metal oxide sensors take a long time to regenerate.

Accordingly, there is a need for a low-cost, fast-response, and high-sensitivity carbon monoxide sensor for use in self-cleaning ovens and other carbon monoxide emitting devices.

As noted above, another application for carbon monoxide sensors is in connection with fuel cells. Fuel cells are known devices that convert chemical energy of a fuel to electrical energy. Each fuel cell includes a pair of electrodes arranged across an electrolyte. The surface of one electrode is exposed to hydrogen or a hydrogen-containing gaseous fuel and the surface of the other electrode is exposed to an oxygen-containing oxidizing gas. Electrical energy is produced at the electrodes through electrochemical reactions. Typically, an adsorbent is used on the surface of the anode that is exposed to hydrogen or the hydrogen-containing gaseous fuel. One known problem associated with fuel cells is the poisoning of this adsorbent by the adsorption of carbon monoxide.

Therefore, there is also a need for a robust, high-sensitivity carbon monoxide sensor for monitoring the carbon monoxide level of the hydrogen or hydrogen-containing gaseous fuel fed to the anodes of a fuel cell. Again, existing infrared sensors are undesirable due to their high cost and low sensitivity and thin-film metal oxide sensors are disadvantageous due to their slow regeneration time. Thus, there is a need for a robust, high-sensitivity, and economical carbon monoxide sensor for monitoring the concentration of carbon monoxide in the hydrogen-containing fuel fed to the anodes of a fuel cell.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

One embodiment of the present invention satisfies the aforenoted need by providing a carbon monoxide sensor that includes a sensing element, a temperature sensor for measuring the temperature of the sensing element, and a signal processing module coupled to the temperature sensor. The sensing element, includes an adsorbent dispersed over a support material. The adsorbent is capable of exothermically adsorbing carbon monoxide.

In other embodiments, the sensor also includes a heating element. Specifically, the heating element heats the sensing element to a temperature that is at least as high as the desorption temperature of the adsorbed carbon monoxide, resulting in a desorption of the adsorbed carbon monoxide and a regeneration of the adsorbent. The preferred adsorbents are monovalent silver ($Ag^+$), monovalent copper ($Cu^+$), and mixtures thereof. The support material may be zeolite, alumina, silica gel, carbonaceous materials, or mixtures thereof. The sensor may include a permeable membrane support substrate disposed on a front side of the sensing element or upstream of the heating element, temperature sensor, and heating element. The sensor may include a protective membrane disposed behind the sensing element, temperature sensor, and heating element.

In still other embodiments, a reference element includes a non-adsorbing material that does not adsorb carbon monoxide. A second temperature sensor is in contact with the reference element. This second temperature sensor is coupled to the processing module and sends signals indicative of the temperature of the reference element to the processing module. A heating element may also be provided for the reference element, or a single heating element may be employed for both the sensing element and reference element.

The present invention also provides a method of detecting a presence of carbon monoxide in a gas. The method includes exposing a sensing element to a gas that may or may not include carbon monoxide. The sensing element includes an adsorbent dispersed over a layer of a support material. The adsorbent is capable of exothermally adsorbing carbon monoxide. The method also includes adsorbing at least a portion of the carbon monoxide in the gas onto the adsorbent, thereby resulting in an increase in the temperature of the sensing element due to the exothermal adsorption. An increase in the temperature of the sensing element can be used as an indication of a presence of carbon monoxide in the gas being tested.

The novel features of the present invention will become apparent to those of skill in the art upon examination of the following detailed description of the invention or can be learned by practice of the present invention. It should be understood, however, that the detailed description of the invention and the specific examples presented, while indicating certain embodiments of the present invention, are provided for illustration purposes only because various changes and modifications within the scope of the invention will become apparent to those of skill in the art from the detailed description of the invention and claims that follow.

BRIEF DESCRIPTION OF THE DRAWING

The accompanying FIGURE, in which like reference numerals refer to identical or functionally-similar elements throughout the separate views and which are incorporated in and form part of the specification, further illustrate the present invention and, together with the detailed description of the invention, serve to explain the principles of the present invention.

The single FIGURE of the drawing is a schematic cross-sectional view of an exemplary carbon monoxide sensor of one embodiment of the present invention.

Figure 1:
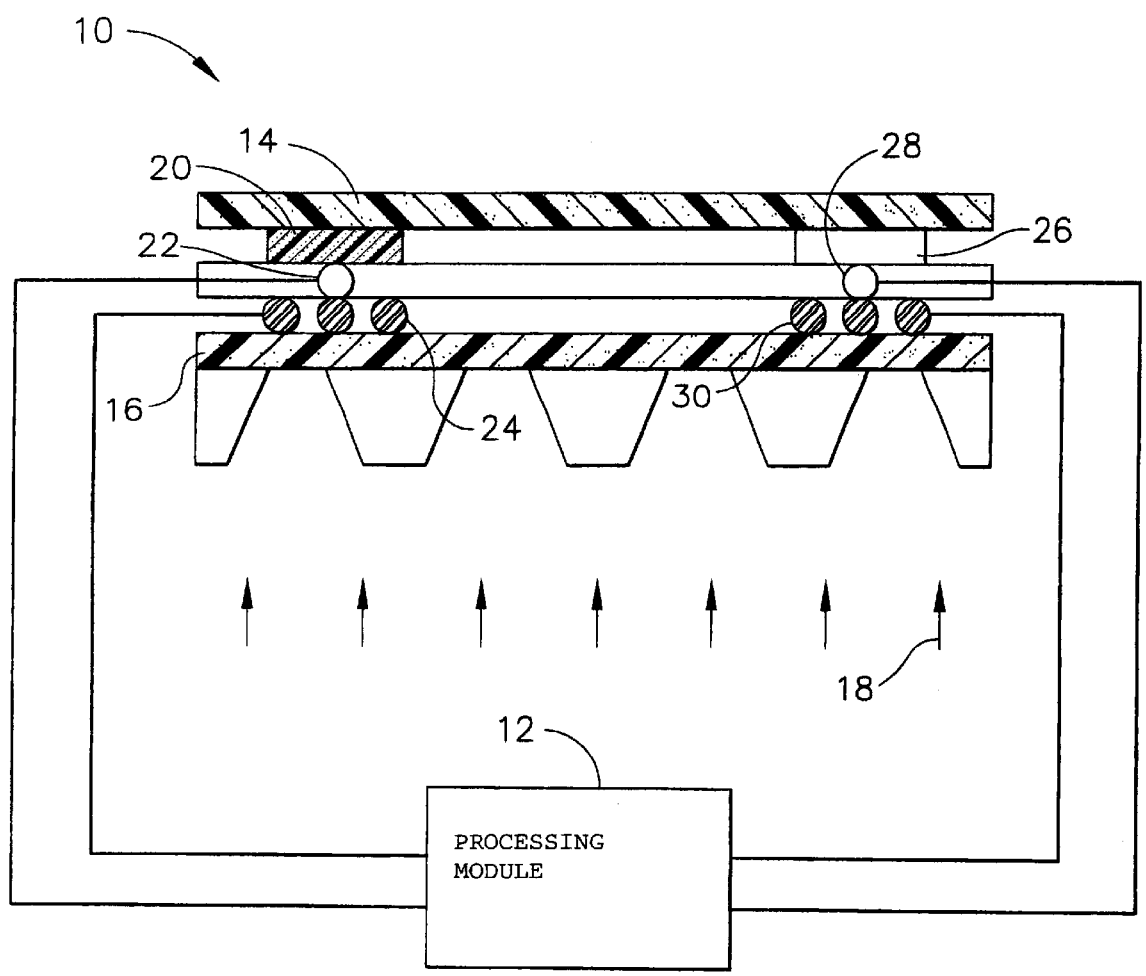

The above and other features and advantages of the present invention will become apparent from the following detailed description of illustrative embodiments, to be read in conjunction with the accompanying drawing.

DETAILED DESCRIPTION OF PREFERRED EMBODIMENTS

The single FIGURE of the drawing illustrates schematically one embodiment of a carbon monoxide sensor 10 made in accordance with the present invention and coupled to a processing module 12. The carbon monoxide sensor 10 includes a protective membrane cover 14 and a permeable membrane 16, which faces the air flow indicated generally by the arrows 18. A carbon monoxide adsorbing layer 20 is disposed between the protective membrane 14 and a temperature probe or sensor 22.

The carbon monoxide adsorbing layer 20 comprises an adsorbent dispersed over a support material. A preferred adsorbent is monovalent copper compounds due to their low cost. However, silver compounds and mixtures of monovalent copper and monovalent silver compounds can also serve as useful adsorbents in the carbon monoxide sensor of the present invention. Suitable support materials include high surface area materials, such as zeolites, alumina, silica gel, carbonaceous materials, and others. The supported $Cu^+$ and/or $Ag^+$ are selective for carbon monoxide in the presence of oxygen, carbon dioxide, methane, nitrogen, and other chemical species.

For example, at 30° C., a NaY-supported CuCl at a loading of 0.554 g CuCl/g NaY will adsorb one millimole of carbon monoxide per gram of adsorber at a concentration of about 100 ppm. The heat of adsorption has been measured to be −48.8 kJ/mole of CO. Good selectivity is observed for carbon monoxide over carbon dioxide, oxygen, methane, and nitrogen. Assuming a sensor area of two hundred by one hundred micrometers and an adsorbent thickness of five micrometers, a highly dispersed $Cu^+$ can adsorb carbon monoxide and provide a temperature rise of 0.1° C. assuming an adsorption time of five seconds. This temperature rise can be used for the sensing of carbon monoxide.

To regenerate the adsorbent or to operate the carbon monoxide sensor 10 at a higher temperature, a heating element 24 is provided. As shown in the single figure of the drawing, the temperature sensor 22 and heating element 24 are coupled to the processing module 12. The temperature sensor 22 and the heating element 24 are preferably provided in the form of a microbridge structure due to their small size, low cost, and high reliability. The details of the microbridge structures will not be repeated here as they are well known to those skilled in the art (see, e.g., U.S. Pat. Nos. 4,478,077; 4,501,144; 4,624,137; 4,651,564; 4,683,159; and 4,696,188).

To improve the accuracy of the carbon monoxide sensor 10, a reference element 26 can be provided. The reference element 26 comprises non-carbon monoxide adsorbing material. A second temperature sensor or reference temperature sensor 28 detects the temperature of the reference element 26. As shown, the reference temperature sensor 28 is also in communication with the processing module 12. Thus, any increase in the ambient temperature can be detected by the reference temperature sensor 28 and the ambient increase in temperature can be deducted from the increase in temperature of the sensing element 20 as sensed by the temperature sensor 22. A separate heating element 30 can also be provided for the reference element 26 or a single element can be provided for purposes of heating the sensing element 20 and reference element 26.

By way of another example, using CuCl dispersed on zeolite and an adsorber size of two hundred by one hundred micrometers by five micrometers, 0.00043 micromoles of carbon monoxide can be adsorbed assuming a selective capacity of ten percent (g/g). Assuming a heat of adsorption of 15 kcal/mole, the total heat that will be released is 27 micro-joules. Assuming a linear uptake of twenty seconds for the adsorption to be completed, the heat rate would be 1.35 microwatts. This corresponds to an estimated temperature rise of 0.027° C.

The electronics used to implement the present invention are known to those skilled in the art. The temperature sensor 22 and heating elements 24, 30 are preferably provided in a micro-bridge structure. The carbon monoxide sensor 10 of the present invention can be manufactured using known microelectromechanical systems (MEMS) technology.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. The description as set forth is not intended to be exhaustive or to limit the scope of the invention. Many modifications and variations are possible in light of the above teaching without departing from the spirit and scope of the following claims. It is contemplated that the use of the present invention can involve components having different characteristics. It is intended that the scope of the present invention be defined by the claims appended hereto, giving full cognizance to equivalents in all respects.

The embodiments of an invention in which an exclusive property or right is claimed are defined as follows:

1. A carbon monoxide sensor comprising:
   a sensing element;
   a temperature sensor;
   a signal processing module in communication with the temperature sensor;
   the sensing element comprising an adsorbent dispersed over a support material, the adsorbent capable of exothermally adsorbing carbon monoxide; and the temperature sensor sending signals indicative of the temperature of the sensing element to the processing module.

2. The carbon monoxide sensor of claim 1 further comprising a heating element to heat the sensing element to a temperature that is at least as high as the desorption temperature of carbon monoxide adsorbed onto the sensing element thereby resulting in an desorption of the carbon monoxide adsorbed by the adsorbent and a regeneration of the adsorbent.

3. The carbon monoxide sensor of claim 2 further comprising a permeable membrane support substrate disposed in front of the sensing element, the temperature sensor, and the heating element.

4. The carbon monoxide sensor of claim 2 further comprising a protective membrane disposed behind the sensing element, the temperature sensor, and the heating element.

5. The carbon monoxide sensor of claim 1 wherein the adsorbent is selected from the group consisting of monovalent $Ag^+$, monovalent $Cu^+$, and mixtures thereof.

6. The carbon monoxide sensor of claim 1 wherein the support material is selected from the group consisting of zeolite, alumina, silica gel, carbonaceous materials, and mixtures thereof.

7. The carbon monoxide sensor of claim 1 wherein the temperature sensor is a first temperature sensor, and wherein the carbon monoxide sensor further comprises:
a reference element comprising a non-adsorbing material that does not adsorb carbon monoxide, and
a second temperature sensor, the second temperature sensor being coupled to the processing module and sending signals indicative of the temperature of the reference element to the processing module.

8. The carbon monoxide sensor of claim 7 wherein the heating element is a first heating element, and wherein the carbon monoxide sensor further comprises a second heating element to heat the reference element.

9. The carbon monoxide sensor of claim 8 wherein the first and second heating elements are in communication with one another.

10. A method of detecting a presence of carbon monoxide in a gas comprising the steps of:
exposing a sensing element comprising an adsorbent dispersed over a layer of a support material to the gas that comprises carbon monoxide, the adsorbent capable of exothermally adsorbing carbon monoxide;
adsorbing at least a portion of the carbon monoxide in the gas onto the adsorbent resulting in an increase in the temperature of the sensing element; and
using the temperature increase of the sensing element thereby indicating the presence of carbon monoxide in the gas.

11. The method of claim 10 further comprising the step of heating the sensing element to a temperature that is at least as high as the desorption temperature of carbon monoxide adsorbed by the adsorbent thereby resulting in a desorption of said carbon monoxide adsorbed by the adsorbent and a regeneration of the adsorbent.

12. The method of claim 10 wherein the sensing element further comprises a temperature sensor and a signal processing module in communication with the temperature sensor.

13. The method of claim 10 wherein the adsorbent is selected from the group consisting of monovalent $Ag^+$, monovalent $Cu^+$, and mixtures thereof.

14. The method of claim 13 wherein the support material is selected from the group consisting of zeolite, alumina, silica gel, carbonaceous materials, and mixtures thereof.

15. The method of claim 10 further comprising the steps of:
exposing a reference element comprising non-carbon monoxide adsorbing material to the gas;
sensing a temperature of the sensing element and a temperature of the reference element; and,
subtracting the temperature of the reference element from the temperature of the sensing element to provide a net temperature increase of the sensing element.

16. A carbon monoxide sensor comprising:
a sensing element comprising an adsorbent dispersed over a support material, the adsorbent capable of exothermally adsorbing carbon monoxide,
a first temperature sensor to sense a temperature of the sensing element,
a reference element comprising a non-adsorbing material that does not adsorb carbon monoxide;
a second temperature sensor to sense a temperature of the reference element;
a signal processing module in communication with the first and second temperature sensors;
the first temperature sensor sending signals indicative of a temperature of the sensing element to the processing module and the second temperature sensor sending signals indicative of a temperature of the reference element to the processing module; and
a heating element to heat the sensing element to a temperature that is at least as high as the desorption temperature of carbon monoxide adsorbed by the adsorbent thereby resulting in a desorption of the carbon monoxide adsorbed by the adsorbent and a regeneration of the adsorbent.

17. The carbon monoxide sensor of claim 16 wherein the adsorbent is selected from the group consisting of monovalent $Ag^+$, monovalent $Cu^+$, and mixtures thereof.

18. The carbon monoxide sensor of claim 16 wherein the support material is selected from the group consisting of zeolite, alumina, silica gel, carbonaceous materials, and mixtures thereof.

19. The carbon monoxide sensor of claim 16 further comprising a permeable membrane support substrate disposed in front of the sensing element, the reference element, the first and second temperature sensors, and the heating element.

20. The carbon monoxide sensor of claim 16 further comprising a protective membrane disposed behind the sensing element, the reference element, the first and second temperature sensors, and the heating element.

21. The carbon monoxide sensor of claim 16 wherein the heating element also heats the reference element.

* * * * *